(12) United States Patent
Rytky

(10) Patent No.: US 8,190,230 B2
(45) Date of Patent: May 29, 2012

(54) ELECTRODE STRUCTURE

(75) Inventor: Pekka Rytky, Oulu (FI)

(73) Assignee: Polar Electro Oy, Kempele (FI)

( * ) Notice: Subject to any disclaimer, the term of this patent is extended or adjusted under 35 U.S.C. 154(b) by 806 days.

(21) Appl. No.: 12/254,958

(22) Filed: Oct. 21, 2008

(65) Prior Publication Data

US 2009/0124881 A1 May 14, 2009

(30) Foreign Application Priority Data

Nov. 12, 2007 (FI) .................................... 20075798

(51) Int. Cl.
*H05K 9/00* (2006.01)
*A61B 5/04* (2006.01)
*A61B 5/0402* (2006.01)

(52) U.S. Cl. ......... 600/388; 600/372; 600/509; 174/350

(58) Field of Classification Search .......... 600/386–392; 174/350, 355, 357, 378, 393, 394
See application file for complete search history.

(56) References Cited

U.S. PATENT DOCUMENTS

| | | | |
|---|---|---|---|
| 4,122,843 A | 10/1978 | Zdrojkowski | |
| 4,763,660 A | 8/1988 | Kroll et al. | |
| 5,752,512 A * | 5/1998 | Gozani | 600/347 |
| 5,782,241 A | 7/1998 | Felblinger | |
| 6,807,438 B1 * | 10/2004 | Brun Del Re et al. | 600/372 |
| 7,176,387 B1 * | 2/2007 | Huang | 174/393 |
| 7,319,895 B2 * | 1/2008 | Klefstad-Sillonville et al. | 600/388 |
| 2002/0026112 A1 | 2/2002 | Nissila et al. | |
| 2004/0073104 A1 * | 4/2004 | Brun del Re et al. | 600/372 |
| 2007/0112344 A1 * | 5/2007 | Keilman | 606/41 |
| 2007/0285868 A1 | 12/2007 | Lindberg et al. | |

FOREIGN PATENT DOCUMENTS

| | | |
|---|---|---|
| CH | 662717 A5 | 10/1987 |
| EP | 0966917 A1 | 12/1999 |
| EP | 1661512 A1 | 5/2006 |
| EP | 1676528 A1 | 7/2006 |
| FI | 20065391 | 12/2007 |
| WO | WO9423648 A1 | 10/1994 |

* cited by examiner

*Primary Examiner* — Lee Cohen
*Assistant Examiner* — Erin M Cardinal
(74) *Attorney, Agent, or Firm* — Hoffmann & Baron, LLP

(57) ABSTRACT

A protective electrode structure comprises a middle protective electrode which resides between an outer protective electrode and the skin electrodes during a measurement. The middle protective electrode and the outer protective electrode are insulated from each other. Additionally, the middle protective electrode may be coupled to a virtual ground of the user-specific performance monitor system.

8 Claims, 4 Drawing Sheets

US 8,190,230 B2

ELECTRODE STRUCTURE

CROSS-REFERENCE TO RELATED APPLICATION

This application claims priority based on Finnish Patent Application No. 20075798, filed Nov. 21, 2007, which is incorporated herein by reference.

BACKGROUND OF THE INVENTION

The invention relates to a protective electrode structure, a measuring device, a garment including the electrode structure and a method of manufacturing the electrode structure.

Description of the Related Art

Vital functions can be measured using a non-invasive performance monitor system. An example of such a measuring system is, for example, a user-specific portable heart rate monitor which measures human heart rate and may comprise as functional units a transmitter unit, a receiver unit and a data transfer unit. The transmitter unit may be equipped with electrodes and worn on the human body, wherein the transmitter unit is usually implemented in the form of a transmitter belt fitted around the chest. The receiver unit refers, for instance, to a watch-like receiver unit which is worn on the wrist, the receiver unit having a telemetric or wired coupling with the transmitter unit. The data transfer unit transfers data received in the receiver unit to a computer, for example. The computer may also control the transmitter unit and the receiver unit via the data transfer unit.

A heart rate measurement is based on monitoring the function of the heart. When the heart beats, it generates a series of electric impulses that can be measured from the body. The measurement and analysis of this signal is called electrocardiography (ECG). The signal itself is called an ECG signal. Different phases of the heart cycle can be discerned in the ECG signal. These are called P, Q, R, S, T and U waves. Other organs or body functions may also be monitored according to similar principles.

The transmitter part located next to the body suffers from electromagnetic interference, and particularly from problems caused by static electricity. When the user moves, the hands and the clothes move near the transmitter unit or even touch it. Synthetic fiber textiles and a dry skin are poor at conducting electricity and attract electric charges, at least before the user starts sweating. In terms of electrical engineering, a great amount of charge at random amplitude and at random frequency then moves in the vicinity of the performance monitor. Such a random movement of a great amount of charge is capacitively coupled to the performance monitor, interfering with its operation.

SUMMARY OF THE INVENTION

An object of the invention is to provide an improved electrode structure. According to an aspect of the invention, there is provided a protective electrode structure for a portable user-specific performance monitor system including skin electrodes for a physiological measurement. The protective electrode structure comprises at least one middle protective electrode configured to protect the skin electrodes against electrical interference and to be placed between an outer protective electrode and the skin electrodes during a measurement, the outer protective electrode being against electrical interference; and the at least one middle protective electrode and the outer protective electrode being insulated from each other.

According to another aspect of the invention, there is provided a measuring device of a user-specific performance monitor system including skin electrodes for a physiological measurement. The measuring device comprises at least one middle protective electrode configured to be placed between an outer protective electrode and the skin electrodes during a measurement; the at least one middle protective electrode and the outer protective electrode being insulated from each other, the outer protective electrode and the at least one middle protective electrode being configured to protect the skin electrodes against electrical interference.

According to another aspect of the invention, there is provided a garment including skin electrodes for a physiological measurement performed by a user-specific performance monitor system. The garment further comprises at least one middle protective electrode configured to be placed between an outer protective electrode and the skin electrodes during a measurement, the outer protective electrode and the at least one middle protective electrode being configured to protect the skin electrodes against electrical interference.

According to another aspect of the invention, there is still provided a method of manufacturing an electrode structure forming at least one middle protective electrode which is placed between an outer protective electrode and the skin electrodes and insulated from the outer protective electrode, the outer protective electrode and the at least one middle protective electrode protecting the skin electrodes against electrical interference.

The invention provides several advantages. The user-specific portable performance monitor system can be protected by lowering the intensity of interference and hence the performance can be improved.

BRIEF DESCRIPTION OF THE DRAWINGS

In the following, the invention will be described in greater detail with reference to the embodiments and the accompanying drawings, in which.

DETAILED DESCRIPTION OF THE EMBODIMENTS

Figure 1:
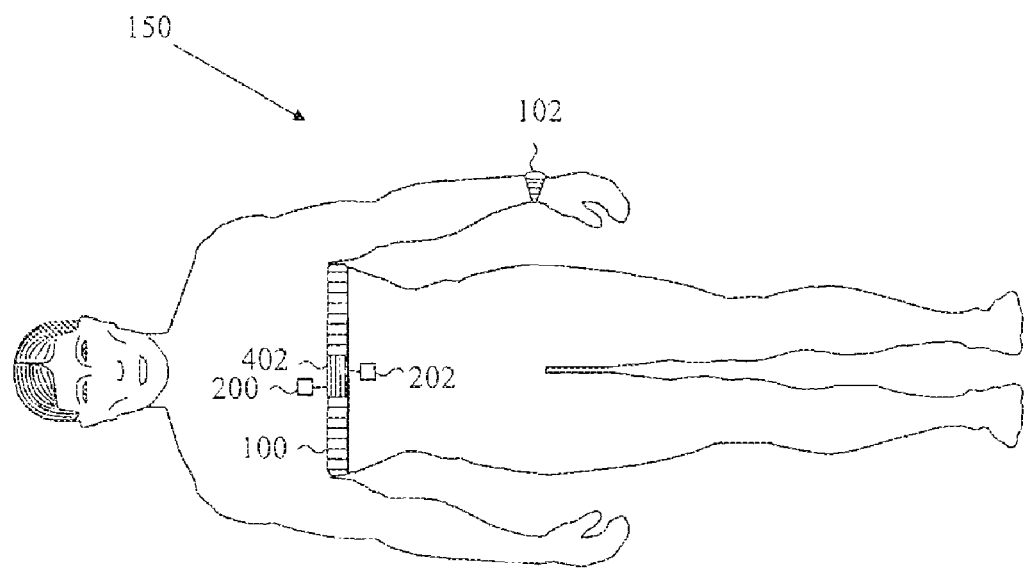
FIG. 1 shows a user-specific performance monitor system.

With reference to an embodiment shown in FIG. 1, a user-specific performance monitor system 150 may comprise two parts. A measuring device 100 which may be like a belt with a potential transmitter may be placed around the chest of a user. Skin electrodes 200, 202 are used to receive a physiological signal from the user and an electronic circuit 402 of the user-specific performance monitor system 150 is used to process and measure the physiological signal. A signal associated with a signal measured by the electrodes of the measuring device 100 may be wirelessly transmitted from the belt to a receiver, which may be implemented as a wristband 102 worn on the wrist of the user. The transmitted signal may carry, for instance, ECG information. The location of the receiver is, however, not restricted to the wrist but may be chosen freely, provided that the wireless communication between the belt and the receiver is possible and the user is capable of operating the receiver. Instead of what is presented in FIG. 1, the belt or the wristband alone may act as a user-specific monitor system 150 which may be a portable heart rate monitor.

In an embodiment, the measuring device 100 may be configured to measure, for instance, a physiological signal such as an electromyogram (EMG) from the user's body.

Figure 2:
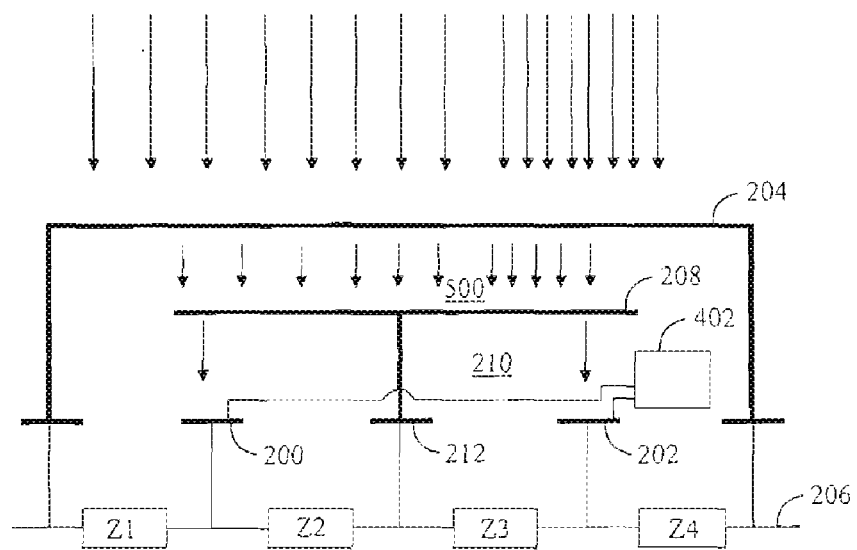
FIG. 2 illustrates a protective electrode structure.

With reference to FIG. 2, examine an example of a protective electrode structure for a user-specific performance monitor system including skin electrodes 200, 202 for a physiological measurement from a body. FIG. 2 presents a pair of skin electrodes, but in general more than two electrodes may be designed for the skin contacts. The skin electrodes are made of electrically conductive material. One of the skin electrodes 200, 202 may be coupled to a virtual ground of the user-specific performance monitor system and a physiological signal may be amplified and measured with respect to the virtual ground. Alternatively, a difference signal detected between the skin electrodes 200, 202 may be amplified and measured with respect to the virtual ground. That prevents a common-mode interference from disturbing the measurement.

The actual measuring device of the user-specific performance monitor system may be protected against electrical interference such as an electric field by an outer protective electrode 204 which may be coupled to the skin 206 outside at least one of the skin contacts of the skin electrodes 200, 202. The outer protective electrode 204 may be a part of the measuring device of the user-specific performance monitor system or it may be (a part of) an outside object.

The arrows illustrate interference of an electric field directed to the measuring device and the density of the arrows show the intensity of the interference. As can be seen, the intensity varies such that interference may be stronger at the right hand side than at the left hand side. The outer protective electrode 204 lowers the intensity of the interference propagating through the outer protective electrode 204 to the middle protective electrode 208. The middle protective electrode 208 of the protective electrode structure may reside between an outer protective electrode 204 and the skin electrodes 200, 202 during a measurement. In general, the protective electrode structure may comprise more than one middle protective electrodes 208.

The at least one middle protective electrode 208 and the outer protective electrode 204 may be electrically insulated from each other. When both the at least one middle protective electrode 208 and the outer protective electrode 204 are, for instance, in the measuring device, an insulating material 210 of measuring device may be used to isolate them. The insulating material 210 may be a polymer or the like.

A middle protective electrode 208 may be coupled to a virtual ground 212 of the user-specific performance monitor system. The virtual ground biases the measurement signals of the skin electrodes to a measurable scale. In general, any protective electrode 204, 208 may be coupled to the skin 206 of a user at a different location or locations than the skin electrodes 200, 202. Impedances Z1 to Z4 separate different contacts to the skin. Hence, the skin electrodes 200, 202 have a measurable dynamic difference in potential.

The outer protective electrode 204 may be a part of the protective electrode structure included in an outside object or in a device which may be the user-specific portable heart rate monitor.

In an embodiment, at least one of the electrodes 200, 202 may be a fabric electrode which readily adapts to the skin surface.

The at least one fabric electrode may be, for example, felt, cloth, textile or tissue. The fabric may be made of a thread of natural or man-made fibers. Furthermore, the fabric may be woven, non-woven or knitted and the fabric may comprise organic or non-organic fibers. The electrical conductivity can be obtained by including conducting fibers and/or threads in the fabric.

The physiological signal from the skin electrodes 200, 202 may be processed and measured in the electronic circuit 402 which may be an analog or a digital processor with an analog-digital converter.

Figure 3:
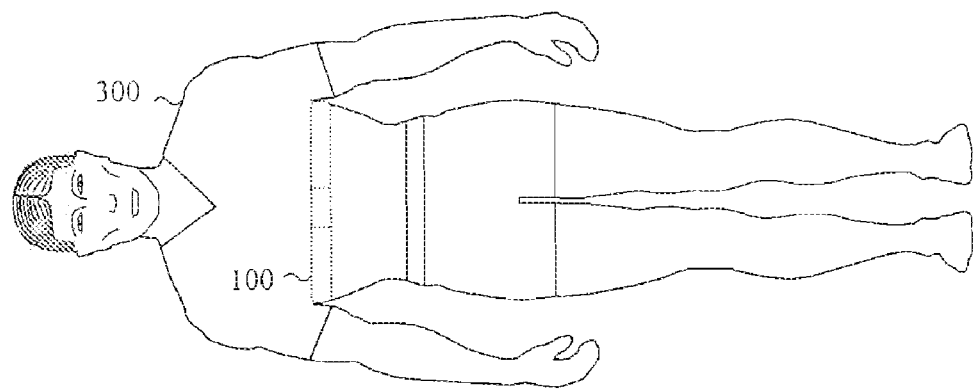
FIG. 3 illustrates a user with a garment.

FIG. 3 shows a user with a garment 300 such as the shirt. The shirt 300 may cover the measurement device 100 of the user-specific performance monitor system. The material of the shirt 300 or a portion of the shirt 300 may be electrically conductive and the shirt may be the outside object including the outer protective electrode 204.

Figure 4:
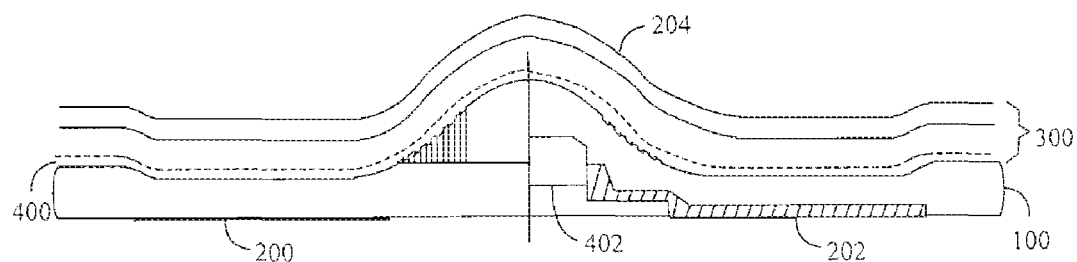
FIG. 4 presents a measuring device under a garment.
Figure 5:
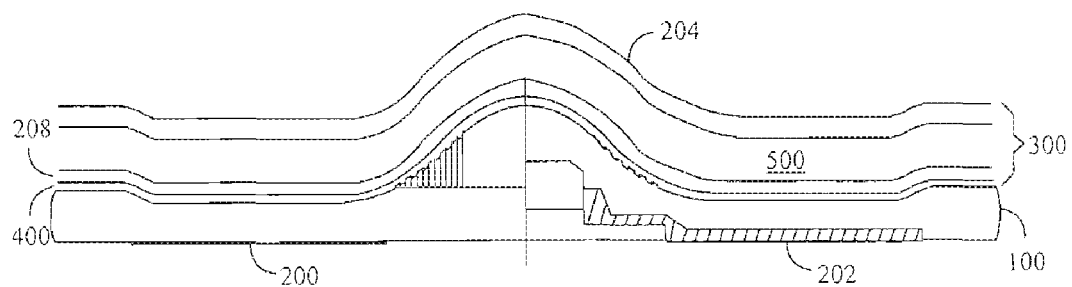
FIG. 5 presents a measuring device under a garment.
Figure 6:
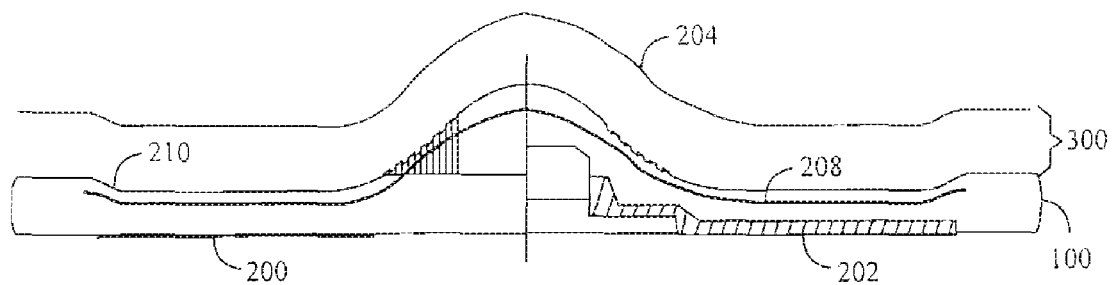
FIG. 6 presents a measuring device under a garment.

FIG. 4 shows a measuring device 100 under the garment 300. The left side shows an external structure of the measuring device 100 and the right side shows an internal structure of the measuring device 100 such as an electronic circuit 402. The shape and the internal structure of the measuring device 100 may vary and hence FIGS. 4 to 6 show only some exemplary sketches. The shirt may have a conductive outer surface which may act as the outer protective electrode 204 which covers the measuring device 100 of the user-specific performance monitor system applied to the body of the user. The measuring device 100 of the user-specific performance monitor system may or may not additionally include at least a part of the protective electrode structure.

Figure 7:
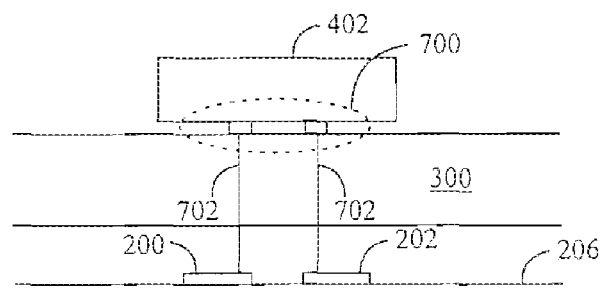
FIG. 7 presents an electrical circuit on a garment.

Instead of what is shown in FIG. 4, the garment 300 may have been fabricated using electrically conductive threads and hence the garment 300 may be thoroughly conductive (see also FIGS. 6 and 7). In the case, the outer surface 400 of the measuring device 100 of the user-specific performance monitor system is electrically insulating. In general, the outer protective electrode 204 may be integrated in a garment, such as a shirt worn by the user. The electrically conductive garment may cover the measuring device 100 of the user-specific portable heart rate monitor during a measurement.

FIG. 5 also shows a garment 300 such as the shirt and the measuring device. In general, the garment 300 may also be, for example, an undervest, a top, a bra or the like. The material of the garment 300 may be felt, cloth, textile, plastic or tissue. The fabric of the garment 300 may be made of a thread of natural or man-made fibers. Furthermore, the fabric may be woven, non-woven or knitted and the fabric may comprise organic or non-organic fibers with and/or without electrical conductivity.

The garment 300 may have a conductive outer surface which may act as the outer protective electrode 204. The surface may be, for example, laminated on the fabric. The garment 300 may also have a conductive inner surface which may act as the middle protective electrode 208. The material 500 of the garment 300 between the inner and the outer surface is electrically insulating for isolating the different electrodes. The garment 300 with the electrodes 204, 208 may cover the measuring device 100 of the user-specific performance monitor system applied to the body of the user. The outer surface 400 of the measuring device 100 of the user-specific performance monitor system is electrically insulating in this case. The measuring device 100 of the user-specific performance monitor system may or may not additionally include at least a part of the protective electrode structure.

FIG. 6 shows the measuring device 100 of the user-specific performance monitor system under the garment 300. The at least one middle protective electrode 208 may be covered by an insulator 210 which may be covered by a garment 300 worn by the user during a measurement. In this example, the garment 300 is thoroughly electrically conductive and forms the outer protective electrode 204. The insulator 210 electrically insulates the at least one middle protective electrode 208 and the outer protective electrode 204 from each other.

FIG. 7 shows an embodiment where the electronic circuit 402 of the measurement device 100 is on the garment 300 instead of being under it. The electric circuit 402 may be fixed to the garment 300, for example, by a press-stud or some other quick-disconnect fitting for a physiological measurement. However, another type of fastening means 700 may also be used. The skin electrodes 200, 202 of the measurement device are in contact with the skin 206 and they may be connected to the fastening means 700 by conductors 702. At least one skin electrode 200, 202 with a respective conductor is insulated from the protective electrodes in the garment 300. In the case of differential signal detection, the skin electrodes 200, 202 are insulated. The fastening means 700 may be used to conduct the physiological signal to the electric circuit 402. The outer protective electrode 204 with the middle protective electrode 208 may be integrated inside the garment 300 in order to protect the skin electrodes 200, 202. In embodiments described in FIGS. 4 to 6 it is also possible to have garments integrated with one or more protective electrodes 200, 202.

The skin electrodes 200, 202 may be integrated to the garment 300. Alternatively, at least one of the skin electrodes 200, 202 may be fastened by, for example, a press-stud or some other quick-disconnect fitting to the garment 300. However, another type of fastening means may also be used.

Figure 8:
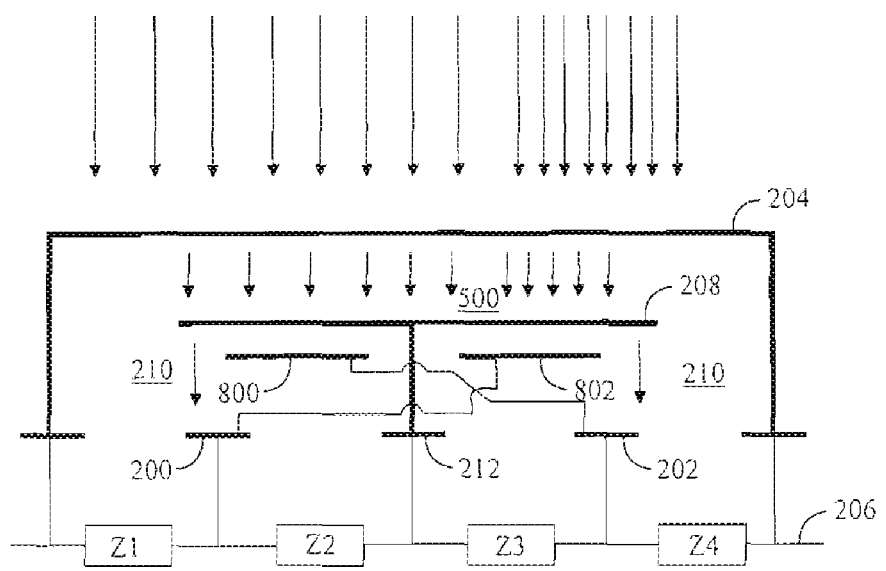
FIG. 8 presents additional protective electrodes.

FIG. 8 shows an embodiment, where the protective electrode structure comprises at least two additional protective electrodes 800, 802. The protective electrodes 800, 802 may be placed between the at least one middle protective electrode 208 and the skin electrodes 200, 202. The additional protective electrodes 800, 802 may overlap half of the skin electrodes 200, 202 and may reach up to the virtual ground electrode 212. The additional protective electrodes 800, 802 are insulated from the at least one middle protective electrode 208 and cross coupled to the skin electrodes 200, 202 such that an additional protective electrode 800 on the left hand side is coupled to a right hand side skin electrode 202 and an additional protective electrode 802 on the right hand side is coupled to a left hand side skin electrode 200. That balances the interference on the skin electrodes 200, 202.

Figure 9:
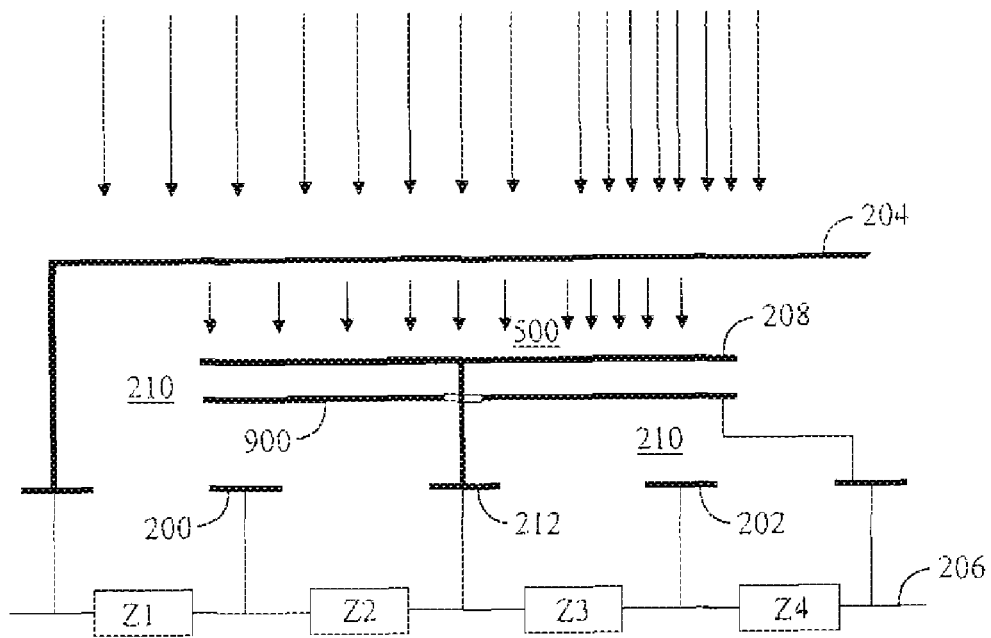
FIG. 9 presents a coupling of additional protective electrodes.

FIG. 9 presents an embodiment where an additional protective electrode 900 is connected to the skin at a separate place from the skin electrodes 200, 202. The additional protective electrode 900 is not in contact with the virtual ground 212.

In embodiments described using FIGS. 8 and 9 it is also possible to have garments integrated with one or more protective electrodes 200, 202, 800, 802, 900.

Figure 10:
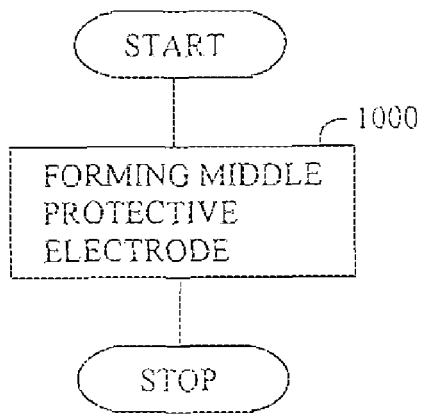
FIG. 10 presents a manufacturing method of the protective electrode structure.

FIG. 10 presents a manufacturing method of the electrode structure. In step 1000, at least one middle protective electrode is formed. The middle protective electrode ought to be placed between an outer protective electrode and the skin electrodes and insulated from the outer protective electrode during a measurement and coupled to a virtual ground of the user-specific performance monitor system.

Even though the invention has been described above with reference to an example according to the accompanying drawings, it is clear that the invention is not restricted thereto but it can be modified in several ways within the scope of the appended claims.

The invention claimed is:

1. A protective electrode structure for a portable user-specific performance monitor system including skin electrodes for a physiological measurement, the protective electrode structure comprising:
    an insulator;
    an outer protective electrode;
    at least one middle protective electrode configured to protect the skin electrodes against electrical interference and to be placed between the outer protective electrode and the skin electrodes during a measurement, the outer protective electrode protecting the skin electrodes against electrical interference, the at least one middle protective electrode and the outer protective electrode being insulated from each other by the insulator, the at least one middle protective electrode being configured to be coupled to a virtual ground of the user-specific performance monitor system; and
    at least two additional protective electrodes configured to balance electrical interference on the skin electrodes and to be placed between the at least one middle protective electrode and the skin electrodes, the additional protective electrodes being configured to be insulated from the at least one middle protective electrode and cross coupled to the skin electrodes.

2. The protective electrode structure of claim 1, wherein the protective electrode structure is included in the user-specific performance monitor system.

3. The protective electrode structure of claim 1, wherein the protective electrode structure is integrated into a garment.

4. The protective electrode structure of claim 1, wherein the at least one middle protective electrode is covered by the insulator which is covered by a garment, which is configured to form the outer protective electrode.

5. The protective electrode structure of claim 1, wherein the middle protective electrode is additionally configured to be coupled to the skin of a user at a different place or places than the skin electrodes.

6. A measuring device of a user-specific performance monitor system including skin electrodes for a physiological measurement, wherein the measuring device comprises:
    an insulator;
    an outer protective electrode;
    at least one middle protective electrode configured to protect the skin electrodes against electrical interference and be placed between the outer protective electrode and the skin electrodes during a measurement, the outer protective electrode protecting the skin electrodes against electrical interference, the at least one middle protective electrode and the outer protective electrode being insulated from each other by the insulator, the at least one middle protective electrode being configured to be coupled to a virtual ground of the user-specific performance monitor system; and
    at least two additional protective electrodes configured to balance electrical interference on the skin electrodes and to be placed between the at least one middle protective electrode and the skin electrodes, the additional protective electrodes being configured to be insulated from the at least one middle protective electrode and cross coupled to the skin electrodes.

7. A garment including skin electrodes for a physiological measurement performed by a user-specific performance monitor system, wherein the garment comprises a protective electrode structure comprising:

an insulator;

an outer protective electrode;

at least one middle protective electrode configured to be placed between an outer protective electrode and the skin electrodes during a measurement, the outer protective electrode and the at least one middle protective electrode being configured to protect the skin electrodes against electrical interference, the at least one middle protective electrode and the outer protective electrode being insulated from each other by the insulator, the at least one middle protective electrode being configured to be coupled to a virtual ground of the user-specific performance monitor system; and at least two additional protective electrodes configured to balance electrical interference on the skin electrodes and to be placed between the at least one middle protective electrode and the skin electrodes, the additional protective electrodes being configured to be insulated from the at least one middle protective electrode and cross coupled to the skin electrodes.

8. A method of manufacturing an electrode structure of a portable user-specific performance monitor system including skin electrodes for a physiological measurement, the method comprising:

forming an insulator;

forming an outer protective electrode;

forming at least one middle protective electrode which is placed between the outer protective electrode and the skin electrodes during a measurement and insulated from the outer protective electrode, the outer protective electrode and the at least one middle protective electrode protecting the skin electrodes against electrical interference, the at least one middle protective electrode and the outer protective electrode being insulated from each other by the insulator, the at least one middle protective electrode being configured to be coupled to a virtual ground of the user-specific performance monitor system; and forming at least two additional protective electrodes configured to balance electrical interference on the skin electrodes and to be placed between the at least one middle protective electrode and the skin electrodes, the additional protective electrodes being configured to be insulated from the at least one middle protective electrode and cross coupled to the skin electrodes.

* * * * *